(12) United States Patent
Allouche et al.

(10) Patent No.: US 11,504,648 B2
(45) Date of Patent: Nov. 22, 2022

(54) WELL CLEAN-UP MONITORING TECHNIQUE

(71) Applicant: Schlumberger Technology Corporation, Sugar Land, TX (US)

(72) Inventors: Francis Allouche, Clamart (FR); Elena Borisova, Clamart (FR)

(73) Assignee: Schlumberger Technology Corporation, Sugar Land, TX (US)

( * ) Notice: Subject to any disclaimer, the term of this patent is extended or adjusted under 35 U.S.C. 154(b) by 734 days.

(21) Appl. No.: 16/336,745

(22) PCT Filed: Sep. 26, 2017

(86) PCT No.: PCT/US2017/053388
§ 371 (c)(1),
(2) Date: Mar. 26, 2019

(87) PCT Pub. No.: WO2018/064020
PCT Pub. Date: Apr. 5, 2018

(65) Prior Publication Data
US 2020/0324224 A1    Oct. 15, 2020

(30) Foreign Application Priority Data
Sep. 27, 2016  (EP) .................................... 16290185

(51) Int. Cl.
*G01F 1/74*   (2006.01)
*E21B 49/08*  (2006.01)
(Continued)

(52) U.S. Cl.
CPC ......... *B01D 17/0214* (2013.01); *B01D 17/12* (2013.01); *C02F 1/40* (2013.01);
(Continued)

(58) Field of Classification Search
CPC ....................... G01N 33/1833; G01N 33/2847
(Continued)

(56) References Cited

U.S. PATENT DOCUMENTS

| 4,429,581 A | 2/1984 | Furmaga et al. |
| 2011/0023595 A1* | 2/2011 | Allouche .................. G01F 1/74 |
| | | 73/152.29 |

(Continued)

FOREIGN PATENT DOCUMENTS

| EP | 0508815 A2 | 10/1992 |
| WO | 2006048418 A1 | 5/2006 |

OTHER PUBLICATIONS

International Preliminary Report on Patentability issued in the related PCT application PCT/US2017/053388, dated Apr. 11, 2019 (8 pages).

(Continued)

*Primary Examiner* — John Fitzgerald
*Assistant Examiner* — Rodney T Frank
(74) *Attorney, Agent, or Firm* — Trevor G. Grove

(57) ABSTRACT

Techniques for monitoring a well clean-up process are disclosed. In one embodiment, a method includes routing a multiphase fluid having oil and water to a separator of a well testing apparatus, separating the multiphase fluid into separate fluids via the separator, and routing the separated fluids away from the separator. The method also includes measuring flow rates of oil and water leaving the separator and determining individual flow rates of oil and water entering the separator as part of the multiphase fluid based on the measured flow rates of oil and water leaving the separator. Additional systems, methods, and devices are also disclosed.

15 Claims, 3 Drawing Sheets

(51) Int. Cl.
    G01F 1/84      (2006.01)
    G01F 23/284    (2006.01)
    G01N 33/28     (2006.01)
    B01D 17/02     (2006.01)
    B01D 17/12     (2006.01)
    C02F 1/40      (2006.01)
    E21B 43/34     (2006.01)
    C02F 101/32    (2006.01)

(52) U.S. Cl.
    CPC .......... *E21B 43/34* (2013.01); *E21B 49/0875* (2020.05); *G01F 1/74* (2013.01); *G01F 1/84* (2013.01); *G01F 23/284* (2013.01); *G01N 33/2847* (2013.01); *C02F 2101/32* (2013.01); *C02F 2209/40* (2013.01)

(58) Field of Classification Search
    USPC ...................................... 73/152.31
    See application file for complete search history.

(56) References Cited

U.S. PATENT DOCUMENTS

| | | |
|---|---|---|
| 2012/0234103 A1 | 9/2012 | Boschi et al. |
| 2012/0253705 A1 | 10/2012 | Chen et al. |
| 2016/0091358 A1 | 3/2016 | Fraser et al. |
| 2016/0273950 A1* | 9/2016 | Henry ................... G01F 15/08 |

OTHER PUBLICATIONS

Partial European Search Report issued in the related EP Application 16290185.4, dated Apr. 11, 2017 (8 pages).

International Search Report and Written Opinion issued in the related PCT application PCT/US2017/053388, dated Jan. 5, 2018 (11 pages).

Extended European Search Report issued in the related EP Application 16290185.4, dated Jul. 17, 2017 (11 pages).

* cited by examiner

WELL CLEAN-UP MONITORING TECHNIQUE

CROSS REFERENCE PARAGRAPH

This application claims the benefit of European Application No. 16290185.4, entitled "WELL CLEAN-UP MONITORING TECHNIQUE," filed Sep. 27, 2016, the disclosure of which is hereby incorporated herein by reference.

BACKGROUND

Field

This disclosure relates generally to hydrocarbon production and exploration and, more particularly, to methods and apparatuses to monitor well clean-up operations.

Description of the Related Art

Wells are generally drilled into subsurface rocks to access fluids, such as hydrocarbons, stored in subterranean formations. The subterranean fluids can be produced from these wells through known techniques. Operators may want to know certain characteristics of produced fluids to facilitate efficient and economic exploration and production. For example, operators may want to know flow rates of produced fluids. These produced fluids are often multiphase fluids (e.g., those having some combination of water, oil, and gas), making measurement of the flow rates more complex. Surface well testing provides various information about the reservoir and its fluids, such as volumetric flow rates of fluids produced from a well and properties of the produced fluids. Surface well testing equipment may be temporarily installed at a wellsite for well test operations and then removed at the conclusion of testing.

Well clean-up is an initial phase of a well test and begins with opening the well. During this phase, non-reservoir fluids, such as completion, drilling, and stimulation fluids, are produced to the surface together with reservoir fluids. At this stage, the effluent composition is not well known, and the flow can be unstable and characterized by a slug flow. Typically, conventional two-phase separators are bypassed during this period. The end of the clean-up can be determined by the value of the basic sediments and water (BSW) in the effluent. In the case of wells that do not produce water, for example, the clean-up phase may be considered finished when the BSW is below 5%, after which a testing phase can start. The well stream is then flowed through the separator. The duration of the clean-up phase can be difficult to predict. The uncertainty is increased when the reservoir water production is high or the reservoir is tight. Hence, it may be useful to monitor the clean-up process to save rig time and expense.

SUMMARY

Certain aspects of some embodiments disclosed herein are set forth below. It should be understood that these aspects are presented merely to provide the reader with a brief summary of certain forms the invention might take and that these aspects are not intended to limit the scope of the invention. Indeed, the invention may encompass a variety of aspects that may not be set forth below.

In one embodiment, a method of operating a well testing apparatus during a well test includes routing a multiphase fluid having oil and water to a separator of the well testing apparatus, separating the multiphase fluid into separate fluids via the separator, and routing the separated fluids away from the separator. The method can also include measuring flow rates of oil and water leaving the separator and determining individual flow rates of oil and water entering the separator, as part of the multiphase fluid, based on the measured flow rates of oil and water leaving the separator.

In another embodiment, a method includes routing a well effluent into a separator through a separator inlet and separating fluids of the well effluent within the separator. The method also includes detecting an interface between separated fluids within the separator and routing the separated fluids out of the separator through separator outlets. Volumetric flow rates at the separator inlet of fluids of the well effluent can then be determined based on the detected interface within the separator and on measured flow rates of the separated fluids routed out of the separator.

In a further embodiment, a well testing apparatus includes a separator having an inlet to receive a multiphase fluid, as well as an oil outlet and a water outlet. The apparatus also includes flow meters for measuring flow rates of fluids leaving the separator through the oil outlet and the water outlet, and a water cut meter for measuring a water cut of fluid leaving the separator through the oil outlet. Additionally, the apparatus includes an analysis system that determines flow rates for oil and water flowing into the separator as part of the multiphase fluid.

Various refinements of the features noted above may exist in relation to various aspects of the present embodiments. Further features may also be incorporated in these various aspects as well. These refinements and additional features may exist individually or in any combination. For instance, various features discussed below in relation to the illustrated embodiments may be incorporated into any of the above-described aspects of the present disclosure alone or in any combination. Again, the brief summary presented above is intended just to familiarize the reader with certain aspects and contexts of some embodiments without limitation to the claimed subject matter.

BRIEF DESCRIPTION OF THE DRAWINGS

So that the manner in which the above recited features can be understood in detail, a more particular description may be had by reference to embodiments, some of which are illustrated in the appended drawings, wherein like reference numerals denote like elements. It is to be noted, however, that the appended drawings illustrate various embodiments and are therefore not to be considered limiting of its scope, and may admit to other equally effective embodiments.

DETAILED DESCRIPTION

Figure 1:
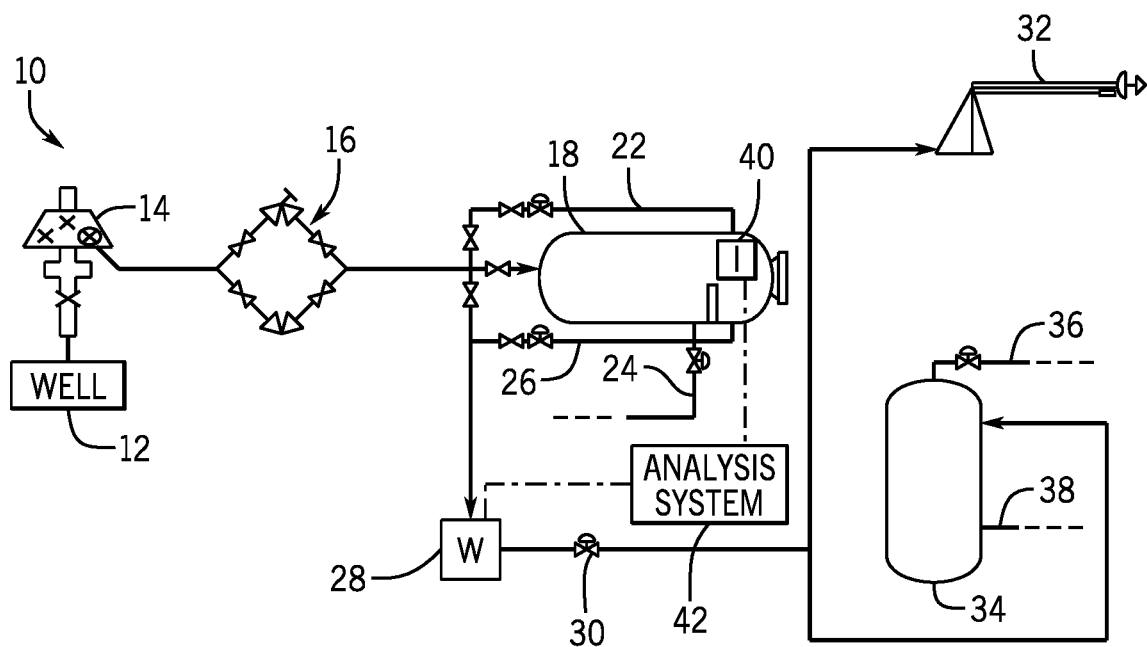
FIG. 1 generally depicts a well testing apparatus at a wellsite in accordance with an embodiment of the present disclosure.

In the following description, numerous details are set forth to provide an understanding of some embodiments of the present disclosure. However, it will be understood by those of ordinary skill in the art that the system or methodology may be practiced without these details and that numerous variations or modifications from the described embodiments may be possible.

In the specification and appended claims: the terms "connect", "connection", "connected", "in connection with", and "connecting" are used to mean "in direct connection with" or "in connection with via one or more elements"; and the term "set" is used to mean "one element" or "more than one element". Further, the terms "couple", "coupling", "coupled", "coupled together", and "coupled with" are used to mean "directly coupled together" or "coupled together via one or more elements". As used herein, the terms "up" and "down", "upper" and "lower", "upwardly" and "downwardly", "upstream" and "downstream"; "above" and "below"; and other like terms indicating relative positions above or below a given point or element are used in this description to more clearly describe some embodiments of the disclosure.

During the clean-up period of a well test, operators routinely perform manual samplings and measurements of BSW at a choke manifold. These measurements can be discrete, operator-dependent, and hardly representative. In some instances, a multiphase flow meter is installed upstream of the separator and used to monitor the fluid flow rates from the first opening of the well. In this way, the clean-up process may be monitored continuously. Multiphase flow meters in such well tests typically provide a complete data set on water, oil, and gas flow rates. A parameter that is used to monitor the clean-up process using a multiphase flow meter is the water-liquid ratio (WLR), which is the fraction of water in the liquid portion of the effluent. It is equal to BSW when no solids are produced from a well.

In some well tests, three-phase separators are used and the effluent may instead be flowed through the separator during the clean-up phase. These separators may allow faster clean-ups (using larger choke sizes) and more environmentally friendly fluid disposal. Separator instrumentation measures pressure, temperature, flow rates at the separator outlets, as well as the gas/liquid (e.g., gas/oil) and liquid/liquid (e.g., oil/water) interfaces in the separator. This data may be acquired in real time. Therefore, the separator may function as a flow metering device and disposal device at the same time.

Certain embodiments of the present disclosure generally relate to well testing operations at a wellsite. More particularly, at least some embodiments relate to monitoring well clean-up operations during well tests. Although BSW measurements are often taken at a sampling point located downstream from a choke restriction (to ensure adequate mixing of the well effluent) and upstream of a separator during well tests, in at least some embodiments of the present disclosure this parameter is estimated from the measurements of flow rates at the separator outlets.

Traditionally, separators have been operated during flow periods where oil and water levels are kept stable. In this case, the outlet flow rates from the separator are equal to the inlet rates. During a clean-up period, however, the flow is unstable, with potentially harsh transients and surges. In accordance with certain embodiments of the present technique, variations of fluid volumes (e.g., amounts of water, oil, and gas) in the separator are used with outlet flow rates to calculate fluid flow rates at the inlet of the separator. In practice, separation within the separator may be imperfect, with some water remaining in fluid exiting the separator through an oil outlet and some oil remaining in fluid exiting the separator through a water outlet, for instance. In some embodiments, such imperfect separation is also accounted for in calculating fluid flow rates at the separator inlet. By way of further example, and as described in greater detail below, a method in accordance with one embodiment can include the use of: a three-phase separator equipped with instrumentation for detection of gas/liquid and liquid/liquid interfaces within the separator; single-phase flow meters; and a water cut meter to determine flow rates for individual phases at the separator inlet. This may enable real-time monitoring of the clean-up process (based on water liquid ratio) and timely decision-making to optimize the duration of the clean-up period, and may also allow the overall cost of operation to be minimized due to the possibility to operate with reduced crew.

Turning now to the drawings, a well testing apparatus 10 is generally depicted in FIG. 1 in accordance with one embodiment. As presently shown, the well testing apparatus 10 (which may also be referred to as a well testing installation) is deployed at a wellsite and connected to receive fluid from a well 12. The well testing apparatus 10 can be deployed at an onshore or offshore wellsite. In offshore contexts, the well testing apparatus 10 can be installed on an offshore drilling rig at the wellsite. The well testing apparatus 10 includes a flowhead 14 that routes effluent from the well 12 through a choke manifold 16 to a separator 18. The well effluent will often be a multiphase fluid, and may include varying amounts of water, oil, and gas produced from the well 12.

The features of the separator 18 can vary between embodiments. For example, the separator 18 can be a horizontal separator or a vertical separator, and can include any of various mechanisms that facilitate separation of components of the incoming effluent, such as diffusers, mist extractors, vanes, baffles, and precipitators to name several examples. In at least some instances, the separator 18 is a three-phase gravity separator that generally separates the multiphase fluid into gas, oil, and water components. The separated gas is routed downstream from the separator 18 through a gas outlet line 22, such as to one or more burners 32 for flaring. Similarly, the separated water is routed downstream from the separator 18 through a water outlet line 24, such as to a water treatment or disposal assembly. Further, the separated oil is routed downstream from the separator 18 through an oil outlet line 26. As shown in FIG. 1, the outlet lines 22, 24, and 26 include control valves that can be operated to control flow of the separated fluids out of the separator 18.

While the separator 18 can be used to separate a received multiphase fluid into individual phases (e.g., water, oil, and gas), those skilled in the art will appreciate that such separation may not be complete. For instance, a multiphase fluid may be separated into water, oil, and gas layers within the separator 18, but the separated water may still include some residual amount of oil. Likewise, the separated oil may still include some amount of water. Still further, the separated gas may include oil or water droplets, and the separated oil and water may include some entrained gas. As used in the present disclosure, and absent some other qualification, any reference to separating fluids, separating a multiphase fluid into separate fluids, or the like includes partial or total separation of a multiphase fluid into individual phases (e.g., water, oil, and gas). The resulting individual phases may be referred to as separated fluids, regardless of whether any of the individual phases retain some amount of one or more other phases.

The well testing apparatus 10 also includes a water cut meter 28 and an additional control valve 30 downstream of the separator 18. Separated oil in the separator 18 can be routed downstream through the water cut meter 28 to one or more burners 32 or fluid tanks 34. The well testing apparatus 10 can include any number of fluid tanks 34, which may be provided in any suitable form, such as vertical surge tanks. In FIG. 1, the tank 34 is shown as receiving fluid from the separator 18 and as having a gas outlet line 36 and a liquid outlet line 38 that allow received fluids to be routed away from the tank 34 to other locations, such as one or more burners 32.

The water cut meter 28 measures the water content of the separated oil (e.g., the volumetric fraction of water in the oil) exiting the separator 18 through the oil outlet line 26. As discussed in greater detail below, this water content of the separated oil measured downstream of the separator 18, such as at the oil outlet of the separator or elsewhere in the oil outlet line 26, can be used in determining flow rates of oil and water into the separator 18 as part of the multiphase well effluent. The water cut meter 28 can be provided at any suitable location that allows receipt of fluid from the separator 18. In some instances, the water cut meter 28 could be connected at the separator 18 itself (e.g., as part of separator instrumentation 40), while in other instances the water cut meter 28 could be positioned further downstream (e.g., on a skid located apart from the separator 18).

The well testing apparatus 10 also includes separator instrumentation 40 and an analysis system 42. As discussed in greater detail below, the separator instrumentation 40 can include various sensors and meters for measuring fluid characteristics. Data acquired via the separator instrumentation 40, the water cut meter 28, and other devices can be used by the analysis system 42 to monitor (and in at least some instances control) the well testing apparatus 10 and a well test procedure. The analysis system 42 can include one or more computer systems or devices. Although generally depicted in FIG. 1 at a wellsite, it is noted that the analysis system 42 could be positioned elsewhere, and could be a distributed system with elements provided at different places near or remote from the well 12. For example, a local component of the analysis system 42 may be located at the wellsite for receiving data from the water cut meter 28 and the separator instrumentation 40, but the received data could be processed by a different portion of the analysis system 42 at another location.

Figure 2:
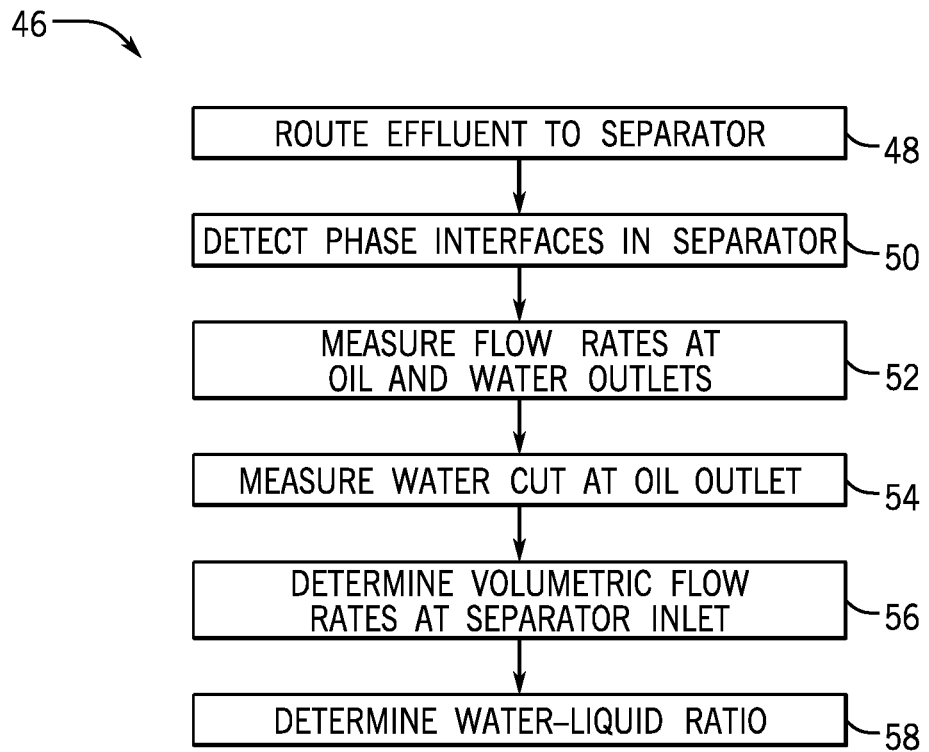
FIG. 2 is a flowchart representing a process for monitoring a well test using a well testing apparatus in accordance with an embodiment of the present disclosure.

Moreover, in at least some embodiments the analysis system 42 uses input from the separator instrumentation 40 and from the water cut meter 28 to determine flow rates of individual phases of the well effluent flowing into the separator 18, such as during a clean-up phase of a well test. One example of a method for operating a well testing apparatus during a well test to determine such flow rates of fluids into the separator 18 is generally represented by flowchart 46 in FIG. 2. In this embodiment, well effluent or other multiphase fluid is routed to a separator (block 48). As noted above, the effluent can separate into individual phases within the separator. More specifically, the various phases can be distributed within the separator by density, with a water layer at the bottom of the separator, an oil layer floating above the water layer, and gas layer above the oil layer.

Phase interfaces between these layers are detected (block 50) within the separator, and flow rates are measured (block 52) for fluids leaving the separator through the oil and water outlets of the separator, as discussed below. In at least some instances, the flow rates for fluids leaving the separator through the oil and water outlets are measured with single-phase flow meters, such as Coriolis meters. The water cut of the fluid exiting the separator through the oil outlet is also measured (block 54). The volumetric flow rates of individual phases within the well effluent entering the separator can then be determined (block 56) using the measured phase interfaces, outlet flow rates, and oil outlet water cut. The method can also include determining the water-liquid ratio of the well effluent entering the separator (block 58). Additional details with respect to this method are provided below.

Figure 3:
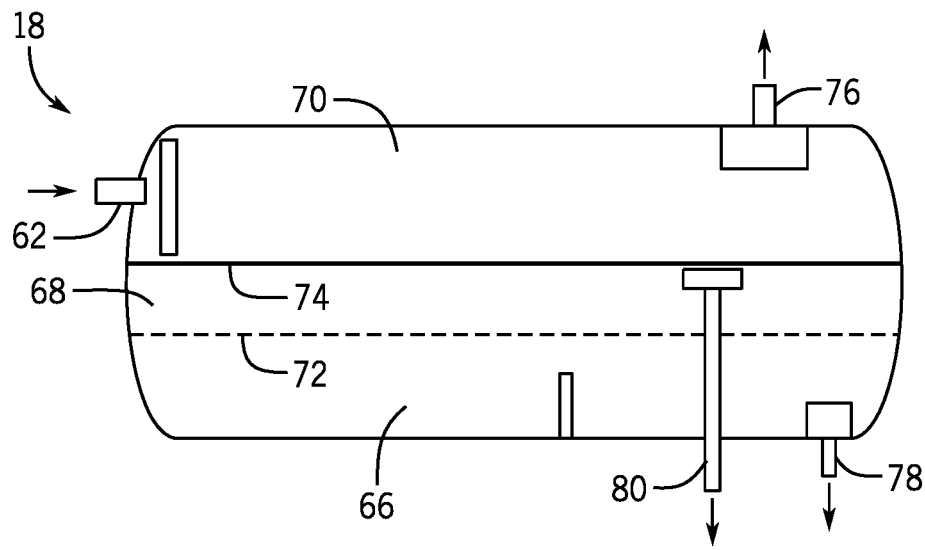
FIG. 3 is a schematic depicting fluid levels in a separator of a well testing apparatus in accordance with an embodiment of the present disclosure.

In some instances the fluids of the well effluent are flowed through the separator 18 and collected in the tank 34 during a clean-up period of a well test. The well effluent may be separated into individual phases within the separator 18, as noted above. An example of this is generally shown in FIG. 3. In this embodiment, the well effluent may be routed into the separator 18 through a separator inlet 62. Inside the separator 18, the effluent may separate into a water layer 66, an oil layer 68, and a gas layer 70. A liquid-liquid interface between the water layer 66 and the oil layer 68 is represented by reference numeral 72 in FIG. 3, and a liquid-gas interface between the oil layer 68 and the gas layer 70 is represented by reference numeral 74. Again, the separator 18 may include any of various mechanisms to facilitate separation, such as an impacting plate near the inlet 62 and a solids weir along the bottom of the separator 18. The gas layer 70 can be routed out of the separator 18 (e.g., into gas outlet line 22) via a gas outlet 76. Likewise, the water layer 66 can be routed out of the separator 18 (e.g., into water outlet line 24) through a water outlet 78, and the oil layer can be routed out of the separator 18 (e.g., into oil outlet line 26) through an oil outlet 80.

Figure 4:
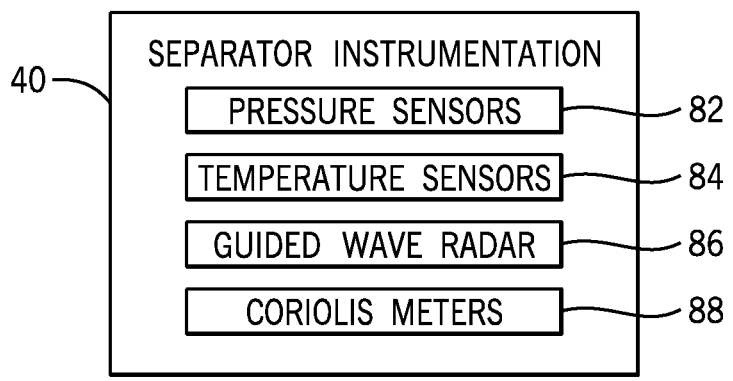
FIG. 4 is a block diagram of components that can be included as separator instrumentation for a separator in accordance with an embodiment of the present disclosure.

The separator instrumentation 40 can include various devices for measuring parameters associated with the separator 18 and the separated fluids. These parameters can include levels of fluids within the separator 18 and flow rates of fluids leaving the separator 18, for instance. As generally represented in FIG. 4 in accordance with an embodiment of the present disclosure, the separator instrumentation 40 includes one or more: pressure sensors 82, temperature sensors 84, guided wave radar devices 86, and Coriolis meters 88. The guided wave radar devices 86 can be used to detect phase interfaces within the separator 18 and to measure the thickness of the oil layer 68 and the total liquid level in the separator 18. In at least some embodiments, the Coriolis meters 88 are provided downstream of the separator outlets and upstream of separator flow control valves of the outlet lines 22, 24, and 26. These Coriolis meters 88 can be used to determine mass flow rates, volumetric flow rates, and densities of the fluids exiting the separator 18 through the separator outlets.

While certain elements of the well testing apparatus 10 are shown in the present figures and discussed above, it is noted that the apparatus 10 may include other components in addition to, or in place of, those presently illustrated and discussed. For example, the well testing apparatus 10 could include a heat exchanger, a surface safety valve, a chemical injection pump, other pumps, and additional manifolds, as well as additional valves (e.g., pressure relief valves of the separator 18 and fluid tank 34). Further, the well testing apparatus 10 could include other measurement devices, such as a gas specific gravity meter, a gas-to-oil ratio sensor, a carbon dioxide sensor, a hydrogen sulfide sensor, or a shrinkage measurement device. These other measurement devices could be provided as part of, or separate from, the separator instrumentation 40. It is also noted that the use of single-phase flow meters (such as the Coriolis meters 88) to measure flow rates at the separator outlets and the subsequent calculation of fluid characteristics (flow rates and water-liquid ratio) at the separator inlet based on the measured outlet flow rates facilitates clean-up monitoring during a well test without a multiphase flow meter upstream of the separator 18 and downstream of the choke manifold 16. Indeed, in at least some embodiments, the well testing apparatus 10 does not include a multiphase flow meter.

During clean-up periods, the positions of the fluid interfaces 72 and 74 in the separator 18 change with time for various reasons. Liquid level set point adjustments can be changed to accommodate increasing amounts of gas. Opening and closing of the control valves and effluent slugging also change the liquid levels. In at least some embodiments of the present techniques, the changes in the liquid levels within the separator 18 are taken into account while using the liquid levels and separator outlet flow rates to estimate production flow rates of fluids at the separator inlet 62.

It is again noted that separation within the separator 18 may not be complete. Therefore, the oil leaving the separator through the oil outlet 80 can contain some amount of water, and water leaving the separator through the water outlet 78 can include some amount of oil. The volumetric fraction of water in the oil exiting the separator 18 via oil outlet 80 can be measured using the water cut meter 28. The amount of oil leaving the water outlet is often very low (from 0 to 2%) and can be neglected as a first approximation in at least some embodiments.

Accordingly, in at least one embodiment having a horizontal separator 18, the volumetric flow rates of oil and water at the separator inlet 62, $Q_o^{inlet}$ and $Q_w^{inlet}$, are estimated using the following equations:

$$Q_o^{inlet} = (1 - \phi_w)\left(A(\alpha)\frac{d\alpha}{dt} - A(\alpha_w)\frac{d\alpha_w}{dt} + Q_{oil\ outlet}\right) \quad (1)$$

$$Q_w^{inlet} = (1 - \phi_w)A(\alpha_w)\frac{d\alpha_w}{dt} + Q_{water\ outlet} + \phi_w\left(A(\alpha)\frac{d\alpha}{dt} + Q_{oil\ outlet}\right) \quad (2)$$

where $A(\alpha) = L_{sep} 2D^2$, $\sqrt{\alpha(1-\alpha)}$, $L_{sep}$ is the internal length of the separator 18, D is the diameter of the separator 18, $\alpha$ is the total level of liquid in the separator 18, $\alpha_w$ is the level of the water layer 66, $Q_{oil\ outlet}$ is the volumetric flow rate at the oil outlet 80, $Q_{water\ outlet}$ is the volumetric flow rate at the water outlet 78, and $\phi_w$ is the volume fraction of water in the oil leaving through the oil outlet 80. The liquid levels $\alpha$ and $\alpha_w$ are normalized by D in this embodiment (e.g., expressed as a fraction of D). As will be appreciated from the description above, the liquid levels $\alpha$ and $\alpha_w$ can be measured with liquid-level sensors of the separator instrumentation 40 (e.g., the guided wave radar devices 86) and the volumetric flow rates $Q_{oil\ outlet}$ and $Q_{water\ outlet}$ can be measured with flow meters. In at least some embodiments, the volumetric flow rates $Q_{oil\ outlet}$ and $Q_{water\ outlet}$ are measured with single-phase flow meters, such as Coriolis meters 88 on the water and oil outlet lines 24 and 26. Further, the water cut $\phi_w$ can be measured with the water cut meter 28, which receives oil routed out of the separator 18 through oil outlet 80.

These estimations of the volumetric flow rates of oil and water into the separator and of the WLR at line conditions can then be re-calculated at standard conditions. In order to re-calculate the fluid rates at line conditions to standard conditions, conventional algorithms could be applied. In most cases, the difference of water properties at line and standard conditions can be neglected, unless a substantial amount of $CO_2$ is produced. Therefore, the volumetric flow rates at standard conditions can be expressed as $$Q_{water}^{std} = Q_w^{inlet} \quad (3)$$

$$Q_{oil}^{std} = Q_o^{inlet}/\alpha_c \quad (4)$$

where $\alpha_c$ is the correction coefficient that accounts for oil shrinkage due to vaporization of gas at lower pressures and thermal contraction. For separator pressures up to 1000 psi, typical oil shrinkage does not exceed 20%, therefore the coefficient $\alpha_c$ can be estimated to vary between 1 (no shrinkage) and 0.8 (maximal shrinkage).

The water-liquid ratio (WLR) at standard conditions is defined as $$WLR^{std} = \frac{Q_{water}^{std}}{Q_{water}^{std} + Q_{oil}^{std}} \quad (5)$$

A threshold value X of WLR can be set to a desired level indicative of the end of a clean-up phase of a well test $$WLR^{std} = \frac{Q_w^{inlet}}{Q_w^{inlet} + Q_o^{inlet}\alpha_c} = X. \quad (6)$$

This criteria can also be expressed in terms of flow rate ratio of water to oil $$\frac{Q_w^{inlet}}{Q_o^{inlet}} = \frac{\alpha_c X}{1 - X}. \quad (7)$$

For example, for an embodiment in which the criteria WLR threshold is equal to 5% (X=0.05), the water/oil flow rate ratio at line conditions should be $$\frac{Q_w^{inlet}}{Q_o^{inlet}} = 0.053 \text{ if } \alpha_c = 1 \quad (8)$$

$$\frac{Q_w^{inlet}}{Q_o^{inlet}} = 0.042 \text{ if } \alpha_c = 0.8 \quad (9)$$

The difference between the thresholds related to different shrinkage is about 0.011, which is very small. Further, the relative error associated with calculation of ratio $$\frac{Q_w^{inlet}}{Q_o^{inlet}}$$

can be estimated from the knowledge of the relative errors on $Q_w^{inlet}$ and $Q_o^{inlet}$. The minimum error on flow rates estimation for $Q_w^{inlet}$ and $Q_o^{inlet}$ corresponds to the case of perfect separation of oil and water in the separator and is estimated to be 5% for each of $Q_w^{inlet}$ and $Q_o^{inlet}$. In this case, the relative error on the ratio of water to oil flow rate is equal to 7%. Therefore, in practice the criteria flow rate ratio for the end of clean-up can be 0.053±0.004 for $\alpha_c$=1 and 0.042±0.003 for $\alpha_c=0.8$. The minimal error on estimation of water to oil ratio represents nearly half of the difference between the threshold values for zero shrinkage and 20% shrinkage. Therefore, the correction for oil shrinkage is comparable to the error on the flow rate ratio estimation. Consequently, correction for oil shrinkage could be neglected in at least some embodiments due to the limits of the measurement accuracy.

Certain assumptions may be made to facilitate the monitoring techniques described above. It will be appreciated that pressure (as well as temperature) of fluids produced from the well 12 can change along the flow path from a maximum (e.g., 750 psi) at the flowhead 14 to nearly atmospheric conditions in the tank 34. Large pressure drops can occur at the flow control devices (e.g., the choke manifold 16 and separator control valves), which can result in changes in the fluid composition. In at least some instances, it can be assumed that the pressure drop and temperature changes between the separator inlet and the separator outlets (e.g., at the location of Coriolis meters, upstream of separator flow control valves) are small enough so that the changes in the vapor-liquid equilibrium are negligible and that the properties of the liquid and gas phases are constant. If some gas evolves out of the oil or liquid condenses out of the gas in the outlet lines, their amount is negligible.

It may also be assumed that the properties of the water-in-oil and oil-in-water dispersions are uniform throughout the separator and its outlets. Under these assumptions, the separator inlet flow rates can be calculated as follows $$Q_o^{inlet} = (1-\phi_w)\frac{dV_o^{sep}}{dt} + (1-\phi_w)Q_{oil\ outlet} + \beta_o\frac{dV_w^{sep}}{dt} + \beta_o Q_{water\ outlet} \quad (10)$$

$$Q_w^{inlet} = (1-\beta_o)\frac{dV_w^{sep}}{dt} + (1-\beta_o)Q_{water\ outlet} + \phi_w\frac{dV_o^{sep}}{dt} + \phi_w Q_{oil\ outlet} \quad (11)$$

where $Q_{oil\ outlet}$ and $Q_{water\ outlet}$ are volumetric flow rates at the oil and water outlets of the separator, respectively; $\phi_w$ is the volumetric concentration of water in the oil outlet; $\beta_o$ is the volumetric concentration of oil in the water outlet; and $V_o^{sep}$ are $V_w^{sep}$ are the volumes of oil and water in the separator.

It is again noted that the water cut meter 28 measures the volumetric concentration of water in the oil outlet, $\phi_w$. In at least some embodiments, the water cut meter 28 is not part of the separator instrumentation 40 and cannot be installed upstream of the separator control valve for the oil outlet line 26. If the water cut meter 28 were installed downstream of the separator control valve for the oil outlet line 26, however, and this control valve were used to control flow through the oil outlet line 26, the fluid properties at the water cut meter 28 may be different from that at the oil outlet 80 of the separator 18. More specifically, strong pressure drop across the control valve could cause some gas to evolve out of the oil. In order to reduce the presence of evolved gas in the measurement section, the separator control valve (or valves) for the oil outlet line 26 is deactivated and kept fully open in at least some embodiments, with the control of the oil level in the separator 18 performed by the one or more additional control valves 30 installed downstream of the water cut meter 28. In this way, the changes of pressure between the separator and the water cut meter 28 measurement section are minimized. Further, it at least some instances, it can be assumed that the pressure drop and temperature changes between the separator and the water cut meter 28 are negligible, and that the amount of any gas present in the measurement section of the water cut meter 28 is also negligible.

Regarding oil-in-water concentration, $\beta_o$, two situations can be distinguished. Typically, the concentration of oil in water is very low (less than 0.1%). In this case, the presence of oil in the water outlet can be neglected, i.e., it can be assumed that $\beta_o=0$. In exceptional situations, oil-in-water concentration could be non-negligible, but will be detectable through density measurement of the Coriolis at the water outlet. Assuming that the concentration of oil in water is negligible (i.e., $\beta_o=0$), the volumetric flow rates at the inlet can be simplified as $$Q_o^{inlet} = (1-\phi_w)\frac{dV_o^{sep}}{dt} + (1-\phi_w)Q_{oil\ outlet} \quad (12)$$

$$Q_w^{inlet} = \frac{dV_w^{sep}}{dt} + Q_{water\ outlet} + \phi_w\frac{dV_o^{sep}}{dt} + \phi_w Q_{oil\ outlet} \quad (13)$$

The volumes of oil and water in the separator can be expressed as functions of their levels. Thus, for a horizontal cylindrical separator, the volumetric flow rates can be expressed as $$Q_o^{inlet} = (1-\phi_w)\left(A(\alpha)\frac{d\alpha}{dt} - A(\alpha_w)\frac{d\alpha_w}{dt} + Q_{oil\ outlet}\right) \quad (14)$$

$$Q_w^{inlet} = (1-\phi_w)A(\alpha_w)\frac{d\alpha_w}{dt} + Q_{water\ outlet} + \phi_w\left(A(\alpha)\frac{d\alpha}{dt} + Q_{oil\ outlet}\right) \quad (15)$$

as indicated in equations (1) and (2) above.

Figure 5:
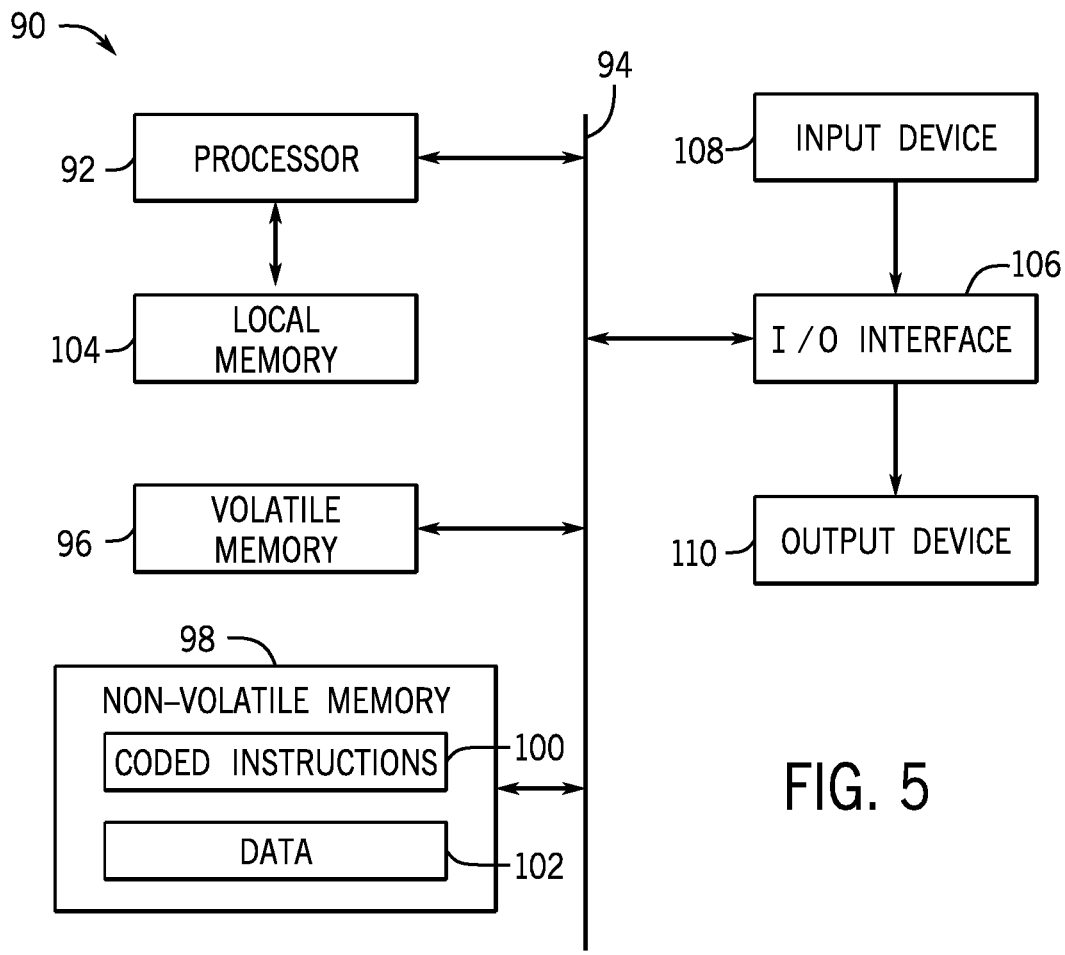
FIG. 5 is a block diagram of components of a processor-based system that can be used to perform certain monitoring operations for a well test in accordance with an embodiment of the present disclosure.

Finally, it is noted that the techniques above can be performed by the analysis system 42, which may be provided as a processor-based system. Such a processor-based system may include a programmable logic controller or programmed general-purpose computer, to name just two examples. One embodiment of a processor-based system 90 is generally provided in FIG. 5. In this depicted embodiment, the system 90 includes at least one processor 92 connected by a bus 94 to volatile memory 96 (e.g., random-access memory) and non-volatile memory 98 (e.g., flash memory). Coded application instructions 100 and data 102 are stored in the non-volatile memory 98. The instructions 100 and the data 102 may also be loaded into the volatile memory 96 (or in a local memory 104 of the processor) as desired, such as to reduce latency and increase operating efficiency of the system 90. The coded application instructions 100 can be provided as software that may be executed by the processor 92 to enable various functionalities, such as determination of flow rates and the WLR of fluids entering the separator 18. In at least some embodiments, the application instructions 100 are encoded in a non-transitory, computer-readable storage medium, such as the volatile memory 96, the non-volatile memory 98, the local memory 104, or a portable storage device (e.g., a flash drive or a compact disc). An interface 106 of the system 90 enables communication between the processor 92 and various input devices 108 and output devices 110. The interface 106 can include any suitable device that enables such communication, such as a modem or a serial port. In some embodiments, the input devices 108 include the water cut meter 28 and the separator instrumentation 40, while the output devices 110 include a storage device or human-machine interface, such as a display or a printer, that enables communication between the system 90 and a user.

The presently disclosed techniques can be used to provide continuous real-time monitoring of the clean-up process during a well test and to enable timely decision making to optimize the duration of the clean-up period, which may reduce the time and expense of the well test. In some instances, such optimization can include detecting a moment when WLR crosses below a threshold indicative of completion of the clean-up process (or detecting a continuous period of time in which the WLR remains below the threshold). The end of the clean-up process could then be confirmed via manual sampling, if desired. The present techniques may also enable a reduction of manual sampling and measurement, which can reduce expense by allowing the well test to be operated with a reduced crew. In at least some embodiments, various measurement components of the well testing apparatus 10 can be operated without field calibration. For instance, single-phase flow meters (e.g., the Coriolis meters 88) and guided wave radar devices 86 may be operated to provide accurate measurements without calibrating these devices at the wellsite. Further, the water cut meter 28 can operate based on microwave resonance and use auto-adjusting correction for oil dielectric properties based on density. The automatic WLR estimation described above may also allow a large reduction in the number of manual BSW measurements at a choke manifold 16. Additionally, in at least some embodiments the automatic measurements are of improved quality (compared to manual measurements), in that they may be continuous, operator-independent, and more representative of the measured fluids. Finally, although certain examples are described above in connection with a well test, the present techniques could also be used to monitor clean-up processes in other instances, such as during a flowback operation after fracturing, during a transition to production, or after workover operations. It will also be appreciated that the well testing apparatus 10 can be used for monitoring clean-up in such other instances.

The foregoing outlines features of several embodiments so that those skilled in the art may better understand aspects of the present disclosure. Those skilled in the art should appreciate that they may readily use the present disclosure as a basis for designing or modifying other processes and structures for carrying out the same purposes or achieving the same advantages of the embodiments introduced herein. Those skilled in the art should also realize that such equivalent constructions do not depart from the spirit and scope of the present disclosure, and that they may make various changes, substitutions and alterations herein without departing from the spirit and scope of the present disclosure.

What is claimed is:

1. A method of operating a well testing apparatus, the method comprising:
   routing a multiphase fluid having oil and water to a separator of the well testing apparatus;
   separating the multiphase fluid into separate fluids via the separator;
   routing the separated fluids away from the separator;
   measuring a flow rate of oil leaving the separator;
   measuring a flow rate of water leaving the separator;
   measuring a level of the water within the separator; and
   determining individual flow rates of oil and water entering the separator as part of the multiphase fluid based on the measured flow rates of oil and water leaving the separator and the level of the water within the separator.

2. The method of claim 1, wherein measuring the flow rate of water leaving the separator includes:
   measuring a flow rate of water leaving the separator through a water outlet of the separator; and
   measuring a flow rate of water leaving the separator through an oil outlet of the separator.

3. The method of claim 2, wherein measuring the flow rate of water leaving the separator through the oil outlet of the separator includes using a water cut meter to determine the proportion of water in fluid leaving the separator through the oil outlet.

4. The method of claim 2, wherein measuring the flow rate of oil leaving the separator includes measuring a flow rate of oil leaving the separator through the oil outlet of the separator.

5. The method of claim 1, comprising measuring an additional level of the water and the oil within the separator.

6. The method of claim 5, wherein determining the individual flow rates of oil and water entering the separator as part of the multiphase fluid is also based on the additional level of the water and the oil within the separator.

7. The method of claim 1, wherein measuring the level of the water within the separator includes using guided wave radar to measure the level of the water within the separator.

8. The method of claim 1, wherein measuring the flow rates of oil and water leaving the separator includes measuring the flow rates of oil and water leaving the separator with Coriolis meters downstream of the separator.

9. The method of claim 1, comprising:
   routing fluid from the separator via an oil outlet of the separator to a water cut meter coupled downstream of the oil outlet; and
   controlling flow of the fluid from the separator via the oil outlet using a control valve positioned downstream of the water cut meter.

10. The method of claim 9, wherein an additional control valve is positioned between the separator and the water cut meter, and routing fluid from the separator via the oil outlet to the water cut meter includes keeping the additional control valve fully open to facilitate flow of the fluid from the separator via the oil outlet to the water cut meter.

11. A well testing apparatus comprising:
    a separator having an oil outlet, a water outlet, and an inlet to receive a multiphase fluid comprising oil and water;
    flow meters coupled to measure flow rates of fluids leaving the separator through the oil outlet and the water outlet;
    a water cut meter positioned so as to measure a water cut of fluid leaving the separator through the oil outlet;
    one or more sensors configured to measure a first level of the water within the separator and to measure a second level of the water and the oil within the separator; and
    an analysis system configured to determine a flow rate, based on the first level of the water within the separator, the second level of the water and the oil within the separator, or both, for the multiphase fluid that is flowing into the separator.

12. The well testing apparatus of claim 11, wherein the one or more sensors configured to measure the first level of the water within the separator and the second level of the water and the oil within the separator are disposed within the separator.

13. The well testing apparatus of claim 11, comprising a fluid tank and a burner coupled downstream of the separator.

14. The well testing apparatus of claim 11, comprising a choke coupled upstream of the separator, wherein the well testing apparatus does not include a multiphase flow meter coupled upstream of the separator and downstream of the choke.

15. The well testing apparatus of claim 11, wherein the well testing apparatus does not include a multiphase flow meter.

\* \* \* \* \*